(12) United States Patent
Kaibel et al.

(10) Patent No.: US 7,476,297 B2
(45) Date of Patent: *Jan. 13, 2009

(54) DEVICE AND METHOD FOR CARRYING OUT HETEROGENEOUSLY-CATALYSED REACTIVE DISTILLATIONS IN PARTICULAR FOR THE PRODUCTION OF PSEUDOIONONE

(75) Inventors: Gerd Kaibel, Lampertheim (DE); Christian Miller, Ruppertsberg (DE); Walter Dobler, Schwetzingen (DE); Thomas Dirnsteiner, Mainz (DE); Marcus Sigl, Mannheim (DE); Helmut Jansen, Dormagen (DE); Björn Kaibel, Hilden (DE)

(73) Assignee: BASF SE, Ludwigshafen (DE)

( * ) Notice: Subject to any disclaimer, the term of this patent is extended or adjusted under 35 U.S.C. 154(b) by 708 days.

This patent is subject to a terminal disclaimer.

(21) Appl. No.: 10/497,520

(22) PCT Filed: Dec. 5, 2002

(86) PCT No.: PCT/EP02/13796

§ 371 (c)(1), (2), (4) Date: Jun. 3, 2004

(87) PCT Pub. No.: WO03/047747

PCT Pub. Date: Jun. 12, 2003

(65) Prior Publication Data

US 2005/0016830 A1    Jan. 27, 2005

(30) Foreign Application Priority Data

Dec. 6, 2001    (DE)  ................................ 101 59 821

(51) Int. Cl.
*B01D 3/32*    (2006.01)
*B01J 8/02*    (2006.01)
*B01J 19/32*    (2006.01)

(52) U.S. Cl. .................. 202/158; 203/29; 203/DIG. 6; 261/112.2; 422/211

(58) Field of Classification Search ................. 202/158; 203/29, DIG. 6; 261/112.2, DIG. 72; 422/211, 422/216, 238, 239
See application file for complete search history.

(56) References Cited

U.S. PATENT DOCUMENTS 5,262,012 A * 11/1993 Smith, Jr. .................... 202/158

(Continued)

FOREIGN PATENT DOCUMENTS

DE    42 01 456    7/1993

(Continued)

OTHER PUBLICATIONS

Derwent Abst. 92-025870/04.

*Primary Examiner*—Virginia Manoharan
(74) *Attorney, Agent, or Firm*—Novak Druce + Quigg LLP

(57) ABSTRACT

A column is described for carrying out reactive distillations in the presence of a heterogeneous particulate catalyst having an ordered packing or random packings which form intermediate spaces in the column interior, the quotient of the hydraulic diameter for the gas flow through the ordered packing or the random packings and the equivalent diameter of the catalyst particles being in the range from 2 to 20, preferably in the range from 5 to 10, in such a manner that the catalyst particles are introduced into the intermediate spaces, distributed and discharged loose under the action of gravity.

16 Claims, 4 Drawing Sheets

U.S. PATENT DOCUMENTS

Figure 1:
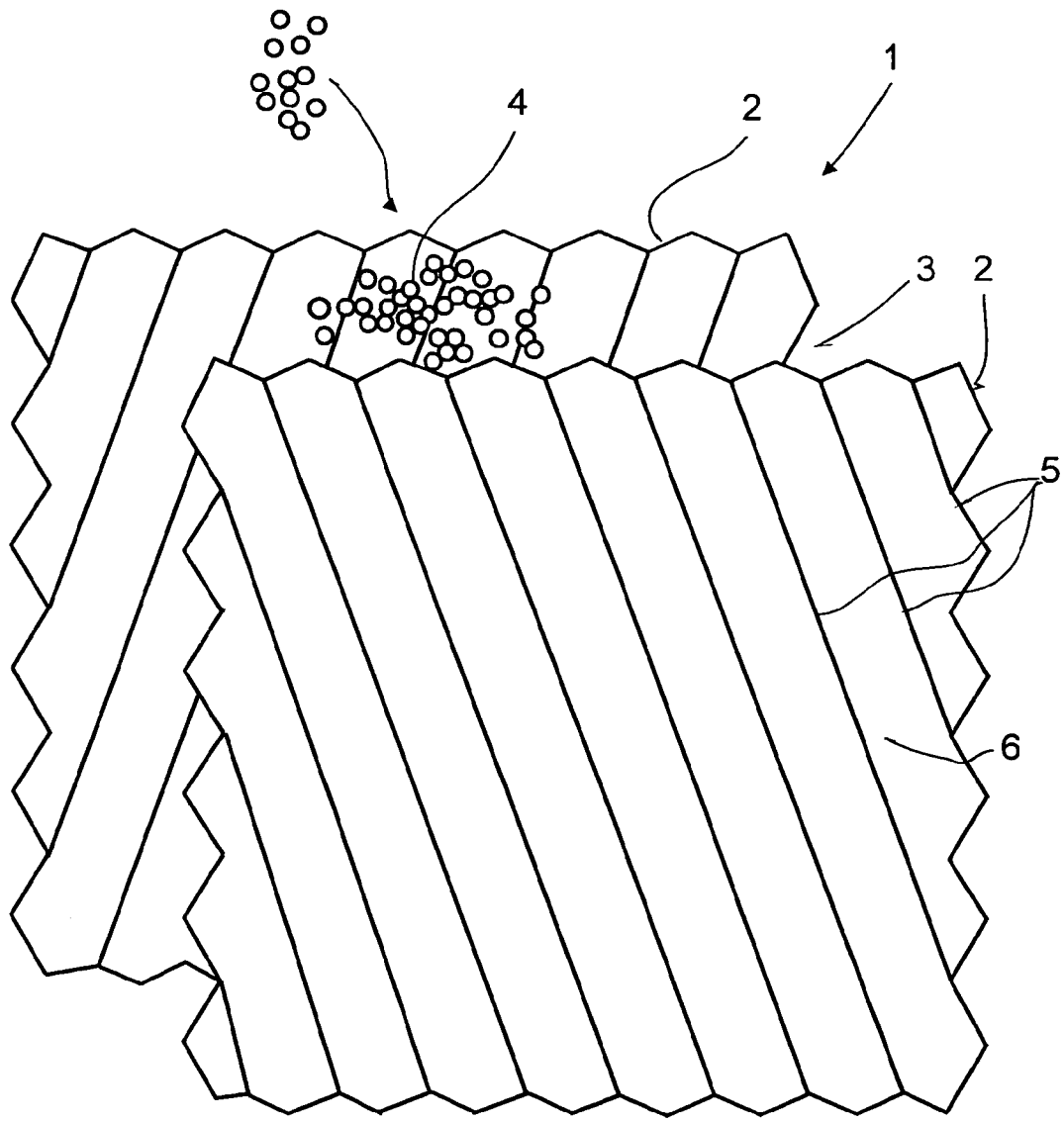

| | | | |
|---|---|---|---|
| 5,275,790 A * | 1/1994 | Buchholz et al. | 422/217 |
| 5,348,710 A * | 9/1994 | Johnson et al. | 422/211 |
| 5,600,053 A | 2/1997 | Girod et al. | |
| 5,730,843 A * | 3/1998 | Groten et al. | 202/158 |
| 6,299,845 B1 | 10/2001 | Romatier et al. | |
| 7,297,249 B2 * | 11/2007 | Kaibel et al. | 208/46 |
| 2002/0038066 A1 | 3/2002 | Strangio et al. | |
| 2003/0224934 A1 * | 12/2003 | Haake et al. | 502/439 |
| 2004/0024273 A1 * | 2/2004 | Bottcher et al. | 585/266 |
| 2007/0287851 A1 * | 12/2007 | Scheidel et al. | 558/355 |

FOREIGN PATENT DOCUMENTS

| | | |
|---|---|---|
| EP | 466 954 | 1/1992 |
| WO | 95/01834 | 1/1995 |
| WO | 99/48604 | 9/1999 |

\* cited by examiner

DEVICE AND METHOD FOR CARRYING OUT HETEROGENEOUSLY-CATALYSED REACTIVE DISTILLATIONS IN PARTICULAR FOR THE PRODUCTION OF PSEUDOIONONE

The invention relates to a column for carrying out reactive distillations in the presence of a heterogeneous particulate catalyst, to a process for reactive distillation, and to a use.

In the prior art, various potential ways are known for carrying out heterogeneously catalyzed reactive distillations, that is to say heterogeneously catalyzed reactions and at the same time separations by distillation in the same column: one possibility is to coat packings of a type known from distillation technology with the active catalyst composition, for example as is the case with KATAPAK-M packing from Sulzer AG, CH8404 Winterthur. A disadvantage in this case is the fact that separate catalyst development is required to prepare active catalyst compositions which can be applied to distillation packings, that the adhesion of the active catalyst compositions to the packings is frequently limited and that relatively limited amounts of active catalyst composition can be applied.

Therefore, columns for reactive distillation are more advantageous which have packings together with particulate catalysts. For this purpose it is known to introduce catalyst particles into pockets of wire mesh which either serve directly as distillation internals, such as the type KATAPAK-S from Sulzer AG, CH8404 Winterthur, or which are designed as flat pockets which are laid between the individual layers of the distillation packings, such as the type Multipak from Montz GmbH, D-40723 Hilden. These designs are also, however, limited with respect to the amount of catalyst which can be accommodated and, in addition, are susceptible to faults in operation, since predetermined liquid flowrates per unit area must be maintained precisely, which is difficult in practice.

The Bales from CDTech, Houston, USA; are of a similar design, but the pocket structures are substantially coarser and therefore the separation efficiencies obtainable are lower. They are described, for example, in EP-A-0 466 954.

All designs having catalyst particles introduced in pockets have in common the fact that filling and removing the catalyst particles is labor-intensive and time consuming.

In contrast, less complex designs are those in which the catalyst is packed onto column trays and is there suspended in the liquid or is accommodated in down columns from the column trays. These embodiments, however, are only suitable for very abrasion-resistant catalysts, which is seldom the case in practice.

It is an object of the present invention to make it possible to use conventional particulate catalysts in reactive distillation columns and so to ensure simple charging of fresh catalyst and discharging of spent catalyst, to reduce mechanical loading of the particulate catalyst by avoiding spouted beds and an excess inherent weight in the case of large bed heights and, furthermore, to homogenize the gas and liquid flows over the column cross section.

We have found that this object is achieved by a column for carrying out reactive distillations in the presence of a heterogeneous particulate catalyst having an ordered packing or random packings which form interstices in the column interior.

In the invention the quotient of the hydraulic diameter for the gas flow through the ordered packing or the random packings and the equivalent diameter of the catalyst particles is in the range from 2 to 20, preferably in the range from 5 to 10, in such a manner that the catalyst particles are introduced into the interstices, distributed and discharged loose under the action of gravity.

It has thus been found that it is possible to charge a column equipped with ordered packings or random packings directly with catalyst particles, without construction of additional reception spaces, for example pockets, being necessary for this.

The hydraulic diameter is defined as is known as the ratio between four times the area through which flow passes and the circumference thereof. Actual calculation of the same for a packing having linear folds is described in the description of the figures in connection with FIG. 2.

The hydraulic diameter of random packings is determined via the porosity of the bed $\psi$, that is to say empty volume of the bed/total volume and the equivalent diameter of the packings, $$d_{hydraulic} = \frac{d_p \times \psi}{1 - \psi},$$

where $d_{hydraulic}$=hydraulic diameter, $d_p$=diameter of the packings and $\psi$=porosity. The equivalent diameter of the packings is defined by the ratio between six times the volume and the surface area of the random packing (see VDI Wärmeatlas [VDI thermal handbook], 5th edition, 1988, Lk 1).

The equivalent diameter of catalyst particles present is defined by the ratio between six times the volume and the surface area of the particle (see VDI Wärmeatlas [VDI thermal handbook], 5th edition, 1988, Lk 1).

Maintaining a quotient of the hydraulic diameter for the gas flow through the ordered packing or the random packings and the equivalent diameter of the catalyst particles within the above defined range ensures according to the invention that the catalyst particles are introduced into the interstices of the ordered packing or the random packings, distributed and discharged loose under the action of gravity.

With respect to the ordered packings or random packings which can be used, there are in principle no restrictions: column internals can be used which are regularly used in distillation technology in order to increase the interfacial area between the phases migrating through the column in countercurrent, the gaseous phase and the liquid phase. The ordered packings or random packings in the column interior form interstices which in principle must be connected to one another to ensure the counterflow of gaseous and liquid phases which is required for the separation action by distillation.

The inventors have thus found that it is possible in principle to introduce catalyst particles into the mutually connected interstices which make up the ordered packing or random packings in the column interior, to distribute them and discharge again the spent catalyst particles loose under the action of gravity.

It must be ensured here that sufficient free interstices are present for the gas flow resulting in distillation, so that there is no backing up of the liquid stream flowing in countercurrent to the gas stream. This is ensured according to the invention by the quotient of the hydraulic diameter for the gas stream through the ordered packing or through the random packings and the equivalent diameter of the catalyst particles being selected very small, that is to say having values in the above defined ranges.

The invention is not limited with respect to the shape and size of the usable catalyst particles; however, to improve the space-time yield of heterogeneously catalyzed reactions, high specific surface areas and thus small catalyst particles are preferred. In beds of catalyst particles, as is known, the pressure drop increases with increasingly smaller catalyst particles and limits, in the case of a reactive distillation, the liquid and vapor throughputs to uneconomically small values. Because of the generally highly pronounced channeling of liquid in catalyst beds, for large column diameters which are required in industrial-scale plants, only low separation efficiencies by distillation are achieved. These disadvantages have prevented hitherto the use, which is desirable per se, of catalyst beds as separation internals in reactive distillations. In contrast, according to the invention, precisely small catalyst particles which are also preferred with respect to catalytic activity, are particularly suitable for combined use with an ordered packing or with random packings, since they are simpler to introduce the smaller are their dimensions compared with the dimensions of the interstices of the ordered packing or random packings.

The catalyst particles are preferably unsupported catalysts, but it is also possible to use supported catalysts. With respect to the shape of the catalyst particles there are in principle no limitations, frequently solid or hollow cylinders, spheres, saddles or honeycomb or star-shaped rods are used. Suitable dimensions of the catalyst particles are, for example for solid cylinder catalyst particles from about 1.5×4 to about 4×8 mm.

According to the invention the interstices which the ordered packing or the random packings make up in the column interior are such that the catalyst particles are introduced into the interstices, distributed and discharged loose under the action of gravity.

Preferably, as column internals, structured packings are used, that is to say ordered packings made up systematically in a regular geometry having defined passage regions for counterflow phases. Ordered packings are generally made up of metal sheets, expanded metal layers or wire mesh layers essentially arranged in parallel to one another. Ordered packings, compared with other column internals, are distinguished by a higher load capacity, improved separation efficiency and a lower specific pressure drop. Packings are generally made up of corrugated metal sheets, expanded metal layers or mesh layers, essentially arranged in parallel to one another, having usually linear corrugations which subdivide the sheet metal packing, the expanded metal layer or mesh layer into corrugated surfaces and in which case the angle of inclination of the corrugated surface to the vertical is usually from 30 to 45°. For the present invention, ordered packings having an angle of inclination of the corrugated surface to the vertical in the range from 10 to 45°, preferably 30°, can be used. By arranging successive ordered packing sheets at the same angle of inclination to the vertical, but with reversed sign, the known cross-channel structures are produced, as are exhibited, for example, by packings of the types Mellapak, CY or BX from Sulzer AG, CH-8404 Winterthur or types A3, BSH, B1 or M from Montz GmbH, D-40723 Hilden.

For use in reactive distillation, preferably, special embodiments of structured packings are used which permit an increased gas flow.

In a particularly preferred embodiment, one or more ordered sheet metal packings of high specific surface area are arranged in alternation with one or more ordered sheet metal packings of low specific surface area. As a result intermediate spaces each having different hydraulic diameter are formed. Particularly preferably, the specific surface areas of the ordered sheet metal packings are chosen in such a manner that firstly intermediate spaces are formed for which the quotient of hydraulic diameter and equivalent diameter of the catalyst particles is <1, and secondly intermediate spaces for which the quotient of hydraulic diameter and equivalent diameter of the catalyst particles is >2, in particular in the above defined range from 2 to 20, in particular from 5 to 10. No catalyst particles are charged into the first-mentioned intermediate spaces having a ratio of hydraulic diameter and equivalent diameter of catalyst particles <1, the same are according to the invention only charged into the intermediate spaces in which said quotient is >2. This particular embodiment ensures an increased gas flow with low pressure drops.

Preferably, the starting material for inventive ordered packings is usually additionally supplied with openings, for example with circular holes of diameter from about 4 to 6 mm, in order to increase the flooding point of the ordered packing and to enable higher column loading. Flooding point of an ordered packing is the volume of gas or liquid per time and per unit area of cross section in which the trickling liquid is backed up or entrained by the gas stream in and above the packing to the point of complete flooding. Exceeding this loading causes a rapid decrease in separation efficiency and a sharp increase in pressure drop.

Instead of ordered packings, equally, random packings can be used, in which case, in principle, there are no limits with respect to the shape of the same. Thus, for example, all shapes of random packings known in distillation technology can be used, such as Raschig rings, Pall rings or saddles.

Ordered packings or random packings which have horizontal surface portions are advantageous. The horizontal surface portions receive some of the weight of the catalyst particles and divert it to the column wall. As a result the mechanical loading of the catalyst is decreased.

Preference is given to ordered packings which are formed from ordered sheet metal packings for vertical installation into the column having linear corrugations which subdivide the ordered sheet metal packing into corrugated surfaces, the angle of inclination of the corrugated surfaces to the horizontal being in the range from 90 to 45°, preferably 60°.

The specific surface area of packings for distillation is from about 250 to 750 $m^2/m^3$. For columns for carrying out heterogeneously catalyzed reactive distillations, ordered packings having lower specific surface areas, in the range from about 50 to 250 $m^2/m^3$ are preferably used.

In the case of ordered packings for distillation, wall thicknesses of the metal sheets of typically from 0.07 to 0.1 mm suffice. In contrast, in the case of heterogeneously catalyzed reactive distillations, depending on catalyst weight and mechanical stability of the catalyst grains, wall thicknesses of the metal sheets in the range from 0.1 to 5 mm, preferably from 0.15 to 0.3 mm, are used.

Preferably, ordered packings or random packings are used which have a reduced resistance to flow at their surface, this reduced resistance to flow being achieved in particular by perforations and/or roughness of the material of the ordered packing or of the random packings or by constructing the ordered packing as expanded metal. The perforations here are preferably dimensioned with respect to their number and dimensions in such a manner that at least a proportion of 20%, preferably a proportion of from 40 to 80%, of the liquid reaction mixture passes through these perforations and flows onto the catalyst particles lying beneath them.

In a preferred embodiment, the ordered packing material consists of expanded metal, the ordered packing material being constructed in such a manner that the liquid flowing off on the packing material as film can flow off as completely as possible through the packing material downward, dripping being reinforced by outlet edges.

Preferably, the perforations are provided in the vicinity of the lower corrugated edges of the ordered sheet metal packings arranged vertically in the column, as described in DE-A 100 31 119. As a result, the fluid is preferably passed onto the upper side of the inclined corrugated surfaces and the liquid loading on the critical lower side is decreased. For this, ordered packings made of ordered sheet metal packings are used for vertical installation into the column having linear corrugations which subdivide the ordered sheet metal packings into corrugated surfaces and which have a width a, measured from corrugated edge to corrugated edge, and perforations, and in which a proportion X of at least 60% of the perforations has a distance b of at most 0.4 a to the lower corrugated edge of each corrugated surface. Preferably, the proportion of the area taken up by the perforations of a corrugated surface is from 5 to 40%, in particular from 10 to 20%, of this corrugated surface.

In a further preferred embodiment, the ordered packing is formed from rippled or corrugated layers, and between two rippled or corrugated layers in each case one flat intermediate layer is disposed, in which case the flat intermediate layers do not extend to the edge of the ordered packing or have, in the edge zone of the ordered packing, an increased gas permeability, in particular holes, in accordance with DE-A 196 01 558.

It is also possible to provide, instead of flat intermediate layers, less intensively rippled or corrugated layers.

The term edge zone of the ordered packing is applied to a concentric volume element which extends from an outer cylinder surface to an inner cylinder surface (the ordered packings typically have a cylindrical shape), with the outer cylinder surface being defined by the outer ends of the rippled or corrugated layers and the inner cylinder surface being defined by the outer ends of the flat layers. The horizontal line connecting the inner cylinder surface to the outer cylinder surface and which is oriented in parallel to the packing layers and passes through the column axis intersects from one to twenty, preferably from three to ten, channels formed by each of the layers disposed next to one another. In the case of flat layers which do not extend into the edge zone, thus up to twenty channels are cleared next to one another in the edge zone. Second layers extending into the edge zone are preferably gas permeable on from 20 to 90% of their surface, particularly preferably from 40 to 60% of their surface, that is to say, for example, provided with holes.

At the points at which the channels formed by the metal sheets contact the column wall, damming of the ascending gas stream occurs, because the channels are closed by the column wall. This leads to a markedly poorer separation efficiency of the ordered packing. By opening the ordered packing channels in the wall zone, this cause of a decreased separation efficiency can be eliminated in a simple and effective manner. The gas can in this case transfer from the channels ending at the column wall into other channels which lead it in the opposite direction.

The invention also relates to a process for reactive distillation in a column which is fitted, as described above, with an ordered packing or random packings together with a bed of catalyst particles. Preferably, the column is operated with respect to its gas and liquid loadings in such a manner that a maximum of from 50 to 95%, preferably from 70 to 80%, of the flooding limit loading is reached.

The invention also relates to the use of the above described column and the process for carrying out heterogeneously catalyzed reactive distillations, in particular acid- or base-catalyzed equilibrium reactions, particularly preferably for preparing pseudoionone by aldolizing citral and acetone in the presence of an aluminum-oxide-supported praseodymium catalyst.

The invention will now be described in more detail below with reference to a drawing and an example.

In the drawings

Figure 2:
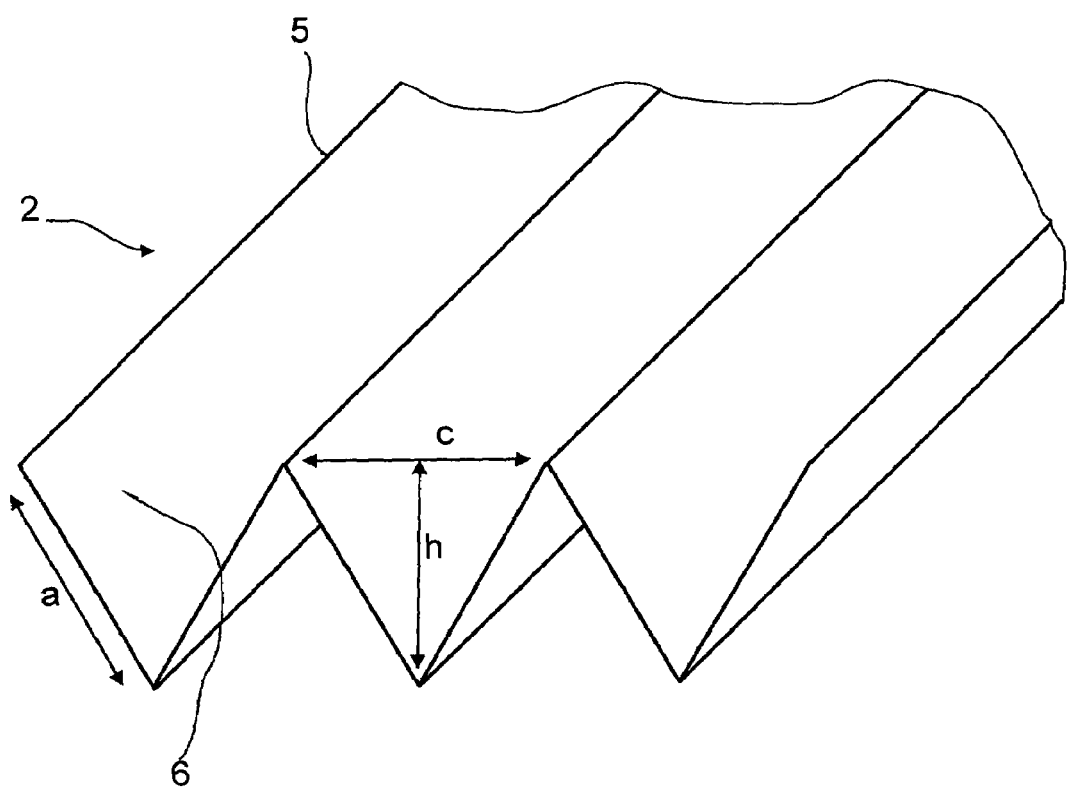
Figure 3:
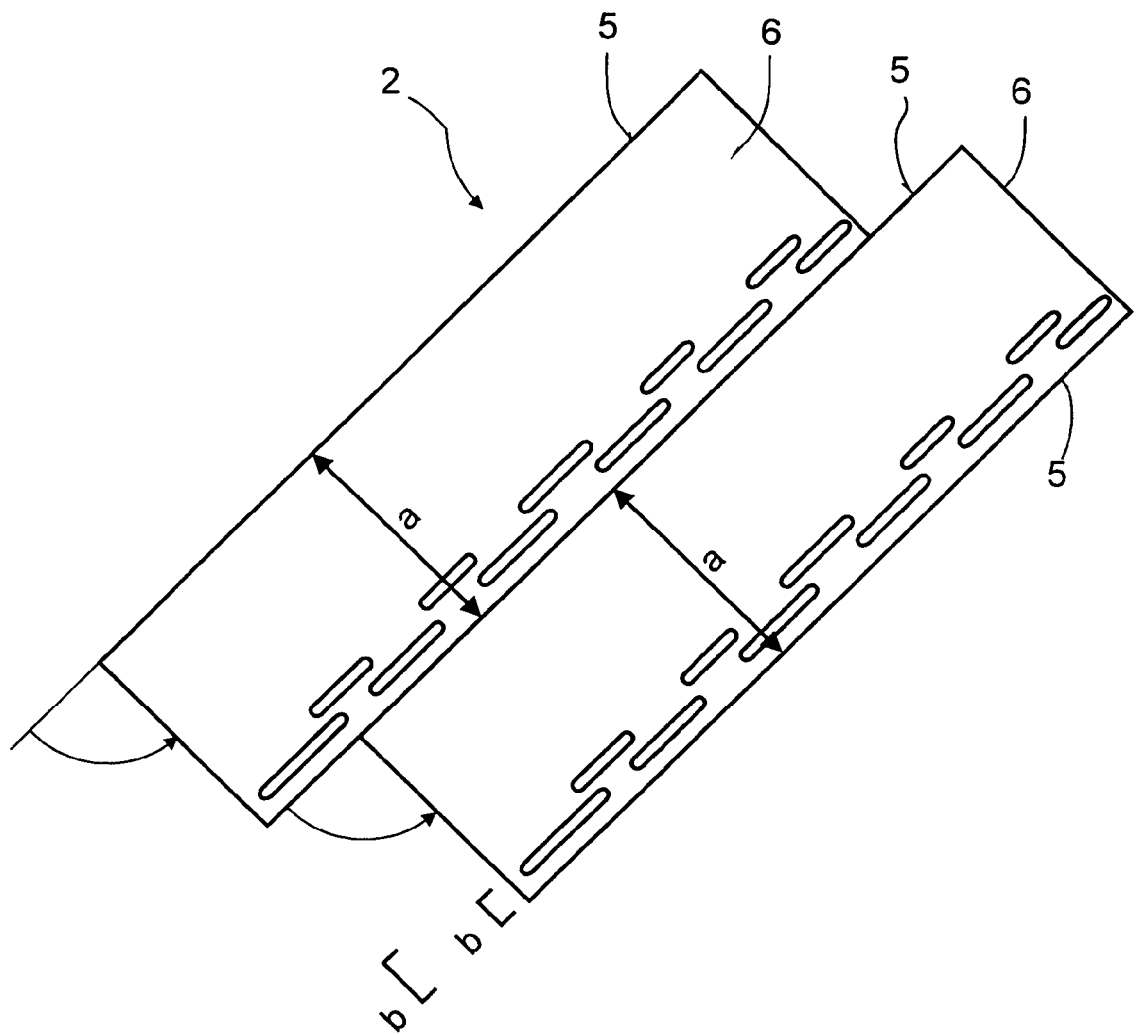
Figure 4:
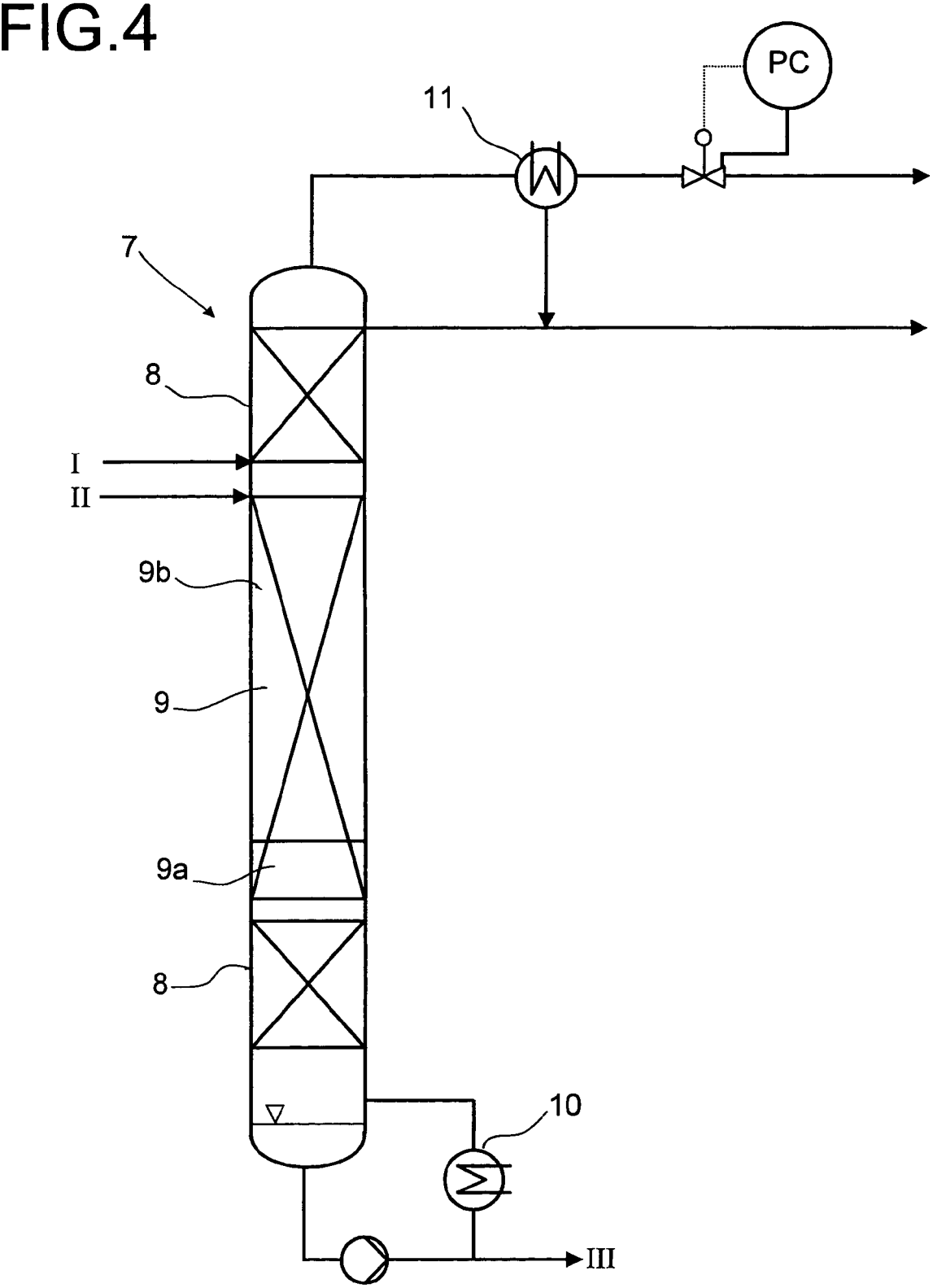

FIG. 1 shows a diagrammatic representation of an embodiment of an inventive ordered packing, FIG. 2 shows a diagrammatic representation of an ordered sheet metal packing having linear corrugations and FIG. 3 shows a diagrammatic representation of an ordered sheet metal packing having perforations and FIG. 4 shows a diagrammatic representation of an embodiment of an inventive column.

The diagrammatic representation in FIG. 1 shows an ordered packing 1 having ordered sheet metal packings 2 which have linear corrugations 5 with formation of corrugated surfaces 6, with in each case an intermediate space 3 being formed between two sequential ordered sheet metal packings 2. According to the invention catalyst particles 4 are charged into the same intermediate space.

FIG. 2 shows diagrammatically an ordered sheet metal packing 2 having linear corrugations 5 and corrugated surfaces 6. a is the width of a corrugated surface 6 measured from corrugated edge 5 to corrugated edge 5, c represents the distance between two adjacent corrugated edges 5 and h represents the height of a corrugation.

FIG. 3 shows diagrammatically a particular embodiment of an ordered sheet metal packing 2 having corrugated edges 5, corrugated surfaces 6 and a width a of the corrugated surfaces 6 having perforations which have a distance b from the lower corrugated edge 5 of each corrugated surface 6.

The reactive distillation column 7 shown diagrammatically in FIG. 4 has two pure separation zones 8, respectively in the upper and lower region of the reactive distillation column 7, which are fitted with structured fabric packings. In the middle column region is arranged a reaction zone 9 which has a lower region 9a containing an ordered packing without introduced catalyst particles and an upper region 9b containing an inventive packing having introduced catalyst particles. The reactive distillation column 7 is fitted with a bottoms reboiler 10 and a condenser 11 at the column top. The starting materials are applied in the upper region of the column as streams I and II, the reaction mixture is taken off as bottom stream III and a top stream IV is taken off at the column top. A pressure controller PC is disposed at the column top.

EXAMPLES

Example 1

Loose Packing Experiments

A column section having a diameter of 0.3 m was fitted with two ordered distillation packings arranged offset by 90° of type B1 from Montz, the height of each ordered packing being 23 cm. Catalyst particles were introduced by loose packing into the ordered distillation packings. The fed volume and the ease of handling during introduction and removal of the catalyst particles were determined. The catalyst particles used were solid cylinders of $\gamma$-$Al_2O_3$ and $TiO_2$. The solid $\gamma$-$Al_2O_3$ cylinders of a diameter of 1.5 mm and a height of from 1 to 4 mm have an equivalent particle diameter of 2 mm. The solid $TiO_2$ cylinders of a diameter of 4 mm and a height of from 2 to 10 mm have an equivalent particle diameter of 5 mm.

1A) Loose packing experiments using solid γ-Al₂O₃ cylinders, diameter 1.5 mm. Ordered packings of type B1 from Montz each having different specific surface areas and different angles of inclination of the corrugated surfaces to the horizontal were used.

1A₁) A sheet metal packing of type B1-125.80 having a specific surface area of 125 m²/m³ and an angle to the horizontal of 80° was used. 90% of the superficial volume was packed with the abovementioned catalyst particles. The ordered packing had a hydraulic diameter of 19 mm. The catalyst was able to be introduced very readily and in the dry state also trickled out again completely. The ratio of the equivalent diameter of the catalyst particles to the hydraulic diameter of the ordered packing was 9.

1A₂) An ordered packing of type B1-250.80 having a specific surface area of 250 m²/m³ and an angle to the horizontal of 80° was packed with the abovementioned catalyst particles. In this case 80% of the superficial volume was able to be packed with catalyst particles. The ordered packing had a hydraulic diameter of 9.4 mm. The catalyst was able to be introduced very readily and in the dry state also trickled out again completely. The ratio of equivalent diameter of the catalyst particles to the hydraulic diameter of the ordered packing was 4.7.

1A₃) A packing of type B1-250.60 was used, that is to say having a specific surface area of 250 m²/m³ and an angle of 60° to the horizontal. 80% of the superficial volume of the same was able to be packed with the abovementioned catalyst particles. The ordered packing had a hydraulic diameter of 9.4 mm. The catalyst was able to be introduced very readily and in the dry state also trickled out again completely. The ratio of the equivalent diameter of the catalyst particles to the hydraulic diameter of the ordered packing was 4.7.

1B) Solid TiO₂ cylinders, diameter 4 mm The above described ordered sheet metal packings of type B1-125.80 and B1-250.60 were used.

1B₁) An ordered sheet metal packing of type B1-125.80, that is to say having a specific surface area of 125 m²/m³ and an angle of 80° to the horizontal was packed with the abovementioned catalyst particles to fill 80% of the superficial volume. The ordered packing had a hydraulic diameter of 19 mm. The catalyst was able to be introduced very readily and in the dry state also trickled out again completely. The ratio of the equivalent particle diameter of the catalyst particles to the hydraulic diameter of the ordered packing was 4.5.

1B₂) An ordered packing of type B1-250.60, that is to say having a specific surface area of 250 m²/m³ and an angle of 60° to the horizontal was packed with the abovementioned catalyst particles to fill 50% of its superficial volume. The ordered packing had a hydraulic diameter of 9.4 mm. The catalyst was able to be introduced very readily and in the dry state also trickled out again completely. The ratio of the equivalent diameter of the catalyst particles to the hydraulic diameter of the ordered packing was 2.4.

In contrast, in the case of commercially conventional catalyst packings in which the catalyst is introduced in pockets, for example of the type Katapak from Sulzer or Multipack from Montz, only from 20 to 30% of the superficial volume, in exceptional cases, a maximum of 50% of the superficial volume, could be packed with catalyst.

Example 2

Pressure Drop Measurements

In a column section of diameter 0.1 m, pressure drop measurements were made using the test mixture nitrogen/isopropanol. For this, the catalyst bed was introduced into the column section and irrigated (one drip position) with a defined amount of isopropanol. In countercurrent to this, a defined amount of nitrogen was passed through the ordered packing/bed from bottom to top. In the experiments the specific pressure drop per unit height of ordered packing or bed was measured and the flooding point was determined. The catalyst particles used were solid γ-Al₂O₃ cylinders. The solid cylinders (d=1.5 mm, h=1-4 mm) had an equivalent particle diameter of 2 mm. The specific pressure drop and the flooding point of a bed introduced into a structured packing were then determined.

Example 2

Comparative Example

B01/0732PCBR

At a bed height of 45 cm, at an F factor of 0.038 $Pa^{10.5}$ (corresponding to a gas flow rate of 1 000 l/h) and a liquid loading of 0.178 m³/m²h (corresponding to a liquid flow rate of 1.4 l/h), a specific pressure drop of 3.33 mbar/m was measured. The ordered packing began to flood, at a constant liquid loading of 0.178 m³/m²h from an F factor of 0.0575 $Pa^{10.5}$ (corresponding to a gas flow rate of 1 500 l/h).

Example 2

According to the Invention

Bed introduced into two layers, offset by 90°, of a structured packing of type BS-250.60 from Montz.

At a bed height of 46 cm, at an F factor of 0.038 $Pa^{10.5}$ (corresponding to a gas flow rate of 1 000 l/h) and a liquid loading of 0.178 m³/m²h (corresponding to a liquid flow rate of 1.4 l/h), a specific pressure drop of 1.09 mbar/m was measured. The ordered packing began to flood, at a constant liquid loading of 0.178 m³/m²h from an F factor of 0.114 $Pa^{10.5}$ (corresponding to a gas flow rate of 3 000 l/h). The maximum gas loading could thus be increased by a factor of 2 compared with the bed which was not introduced into an ordered packing.

Below, with reference to FIG. 2, the calculation of the hydraulic diameter for an ordered packing having linear corrugations is described:

The ordered sheet metal packing 2 shown by way of example in FIG. 2 has linear corrugations 5 arranged in parallel to one another, which corrugations subdivide the ordered sheet metal packing 2 into corrugated surfaces 6. The width of a corrugated surface 6, measured from corrugated edge 5 to corrugated edge 5, is designated a, the distance between two sequential corrugated edges 5 is designated c and the height of the corrugation is designated h. The hydraulic diameter of the gas flow for an ordered packing made up of such ordered-sheet metal packings is then calculated using the equation $$d_{hydraulic,gas} = \frac{2c \cdot h}{c + 2a}$$

Example 3

Preparation of Pseudoionone by Aldolization of Citral and Acetone

The experimental set up corresponded to the diagrammatic representation in FIG. 4. The reactive distillation column 7 was packed in each of the separation zones 8 with one segment of a structured fabric packing of type A3-500 from Montz, having a total height in each case of 23 cm. The reaction zone 9 was fitted in the lower region of the same with one layer of Montz-Pak type B1-1000 in a special element height of 30 mm. This layer served as catalyst barrier so that the catalyst particles could not trickle into the lower separation zone. On this layer were installed three layers of Montz-Pak from type B1-250.60 having an element height of 212 mm, into which the catalyst was introduced by loose packing. 3121 g of catalyst were packed in this case at a bulk density of 700 kg/m³. The catalyst used was solid cylinders of 5% praseodymium on γ-Al₂O₃ having a particle diameter of 1.5 mm and a height of from 1 to 4 mm, which had been prepared by impregnating γ-Al₂O₃ with an aqueous solution of praseodymium nitrate and subsequent calcination. The column was fitted at regular intervals with thermocouples and with sampling points, so that the temperature profile and concentration profile in the column could be determined.

The reactants citral and acetone (streams I and II, respectively, in FIG. 4) were metered into the reactive distillation column from reservoir vessels standing on balances, with mass flow controlled by a pump.

The bottoms reboiler 10 which was heated to 124° C. using a thermostat had a holdup from 50 to 150 ml during operation, depending on residence time. The bottoms stream III was transported under level control by a pump from the bottoms reboiler 10 into a vessel standing on a balance.

The overhead stream from the reactive distillation column was condensed in a condenser 11 which was operated using a cryostat. A portion of the condensate passed via a reflux divider, as stream IV, into a reservoir vessel standing on a balance, while the other portion was applied to the column as reflux. The apparatus was equipped with a pressure controller PC and designed for a system pressure of 20 bar. All influent and effluent streams were continuously detected and recorded during the entire experiment using a process control system PCS. The apparatus was operated continuously in 24 hour operations.

A stream I of 220.0 g/h, equivalent to 1.4 mol/h of citral having a purity of 97%, and a stream II of 840.0 g/h, equivalent to 14.32 mol/h of acetone preheated to 80° C. of a purity of 99% were continuously applied to the above described reactive distillative column 7.

Experimental Procedure

The catalyst used in the reaction zone 9 was solid cylinders (d=1.5 mm, h=1-4 mm) of 5% Pr on γ-Al₂O₃. A system pressure of 3 bar and a reflux ratio of 3 kg/kg was set. The bottom temperature was 92.5°. The bottom stream III of the column obtained was 735.6 g/h of crude product containing 62.14% by weight of acetone, 0.71% by weight of water, 0.45% by weight of mesityl oxide, 0.95% by weight of diacetone alcohol, 9.14% by weight of citral, 24.43% of pseudoionone and 2.18% by weight of high boilers. At the top of the column, 323.2 g/h of distillate (stream IV) were taken off, consisting of 95.8% by weight of acetone and 4.2% by weight of water.

Pseudoionone was obtained with a selectivity of 97.3% based on citral and 84.4% based on acetone. The yield was 66.7% based on citral.

At F factors of 0.12 $Pa^{10.5}$ and liquid loadings of 0.3 m³/m²h, a differential pressure of approximately 1 mbar was measured over the column.

When an uncontrolled catalyst bed without ordered packing was used, in comparison twice the pressure drop was measured.

The differential pressure is a measure of the loading (gas and liquid) of the column. Depending on material properties and the type of internals used, the differential pressure increases with increasing loading until flooding occurs. In the flooding state, the catalyst is swirled up and high catalyst abrasion can occur. This state must therefore be avoided.

When the inventive ordered packing is used, therefore, a higher throughput can be achieved for the same column diameter.

We claim:

1. A column, for carrying out reactive distillations in the presence of a heterogeneous particulate catalyst,
    said column comprising a first region and a second region arranged in alternation,
    wherein the first region comprises an ordered packing formed from ordered sheet metal packings, the ordered sheet metal packings of the first region having a specific surface area, the ordered sheet metal packings of the first region forming intermediate spaces in the column interior,
    wherein the second region comprises an ordered packing formed from ordered sheet metal packings, the ordered sheet metal packings of the second region having a specific surface area, the ordered sheet metal packings of the second region forming intermediate spaces in the column interior, and
    wherein the specific surface areas of the ordered sheet metal packings of the first and second regions differ in such a manner that when catalyst particles are introduced into the intermediate spaces of the first region, but not the second region, and when a gas stream is passed through the column,
    a quotient of hydraulic diameter and equivalent diameter of the catalyst particles present in the first region is in the range from 2 to 20,
    the catalyst particles are distributed between the first and second region and discharged loose under the action of gravity, and
    a quotient of hydraulic diameter and equivalent diameter of the catalyst particles present in the second region is less than 1.

2. A column as claimed in claim 1, wherein the ordered packing is a structured packing.

3. A column as claimed in claim 2, wherein the structured packing is a cross-channel packing.

4. A column as claimed in claim 2, wherein the ordered packing is formed from rippled or corrugated layers, and between two rippled or corrugated layers in each case one flat intermediate layer is disposed, with the flat intermediate layers not extending to the edge of the ordered packing or having, in the edge zone of the ordered packing, an increased gas permeability.

5. A column as claimed in claim 4, wherein the increased gas permeability in the edge zone of the ordered packing is due to holes.

6. A column as claimed in claim 2, wherein the ordered packing is formed from ordered sheet metal packings for vertical installation into the column having linear corrugations which subdivide the ordered sheet metal packings into corrugated surfaces and which have a width a, measured from corrugated edge to corrugated edge and perforations, wherein a proportion X of at least 60% of the perforations has a distance b of at most 0.4 a to the lower corrugated edge of each corrugated surface.

7. A column as claimed in claim 1, wherein the ordered packing has horizontal surface portions.

8. A column as claimed in claim 7, wherein the ordered packing is formed from ordered sheet metal packings,
   wherein the ordered sheet metal packings are adapted for vertical installation into the column,
   wherein the ordered sheet metal packings have linear corrugations which subdivide the ordered sheet metal packing into corrugated surfaces,
   wherein the ordered sheet metal packings have horizontal surface portions, and
   wherein an angle of inclination between the corrugated surfaces and the horizontal surface portions is in the range from 90° to 45°.

9. A column as claimed in claim 8, wherein the angle of inclination of the corrugated surfaces to the horizontal is 60°.

10. A column as claimed in claim 1, wherein the ordered packing has a reduced resistance to flow at its surface.

11. A column as claimed in claim 10, wherein the reduced resistance to flow at the surface of the ordered packing is due to perforations and/or roughness of the material of the ordered packing or by constructing the ordered packing as expanded metal.

12. A process for reactive distillation in a column as claimed in claim 1, which comprises operating the column with respect to its gas and liquid loadings in such a manner that a maximum of from 50 to 95% of the flooding limit loading is reached.

13. A process as claimed in claim 12, wherein the reactive distillation is a heterogeneously catalyzed reactive distillation.

14. A process as claimed in claim 13, wherein the heterogeneously catalyzed reactive distillations are acid- or base-catalyzed equilibrium reactions.

15. A process as claimed in claim 14, wherein the heterogeneously catalyzed reactive distillation is the preparation of pseudoionone by aldolizing citral and acetone in the presence of an aluminum-oxide-supported praseodymium catalyst.

16. A column as claimed in claim 1, wherein the specific surface areas of the ordered sheet metal packings of the first and second regions differ in such a manner that when catalyst particles are introduced into the intermediate spaces of the first region, but not the second region, and when a gas stream is passed through the column, a quotient of hydraulic diameter and equivalent diameter of the catalyst particles present in the first region is in the range from 5 to 10.

* * * * *